United States Patent [19]

Anapliotis et al.

[11] Patent Number: 4,595,393
[45] Date of Patent: Jun. 17, 1986

[54] HIP JOINT PROSTHESIS HAVING A HOLLOW SHAFT

[75] Inventors: Emmanuel Anapliotis; Curt Kranz, both of Berlin, Fed. Rep. of Germany

[73] Assignee: Mecron Medizinische Produkte GmbH, Berlin, Fed. Rep. of Germany

[21] Appl. No.: 554,641

[22] Filed: Nov. 23, 1983

[51] Int. Cl.⁴ .............................................. A61F 1/04
[52] U.S. Cl. ................................. 623/22; 128/92 C; 128/92 CA
[58] Field of Search ................... 3/1.9, 1.91, 1.911, 3/1.912, 1.913; 128/92 C, 92 CA, 92 B, 92 BB, 92 BC

[56] References Cited

U.S. PATENT DOCUMENTS

| 3,064,645 | 11/1962 | Ficat et al. ................ 128/92 CA |
| 4,064,567 | 12/1977 | Burstein et al. ................ 3/1.913 |
| 4,287,617 | 9/1981 | Tornier ................ 3/1.913 |

FOREIGN PATENT DOCUMENTS

| 2617749 | 11/1977 | Fed. Rep. of Germany . |
| 2842847 | 4/1980 | Fed. Rep. of Germany ........ 3/1.91 |
| 2941265 | 4/1980 | Fed. Rep. of Germany . |
| 2851598 | 6/1980 | Fed. Rep. of Germany . |
| 2933237 | 3/1981 | Fed. Rep. of Germany . |
| 3006178 | 7/1981 | Fed. Rep. of Germany . |
| 2310121 | 12/1976 | France ............................. 3/1.91 |

OTHER PUBLICATIONS

Morscher et al., "Erste Erfahrungen mit einer zementlosen isoelastischen Totalprothese der Hüfte", Z. Orthop 113 (1975), pp. 745-749.

Primary Examiner—Richard J. Apley
Assistant Examiner—David J. Isabella

[57] ABSTRACT

In a hip joint prosthesis having an elongated hollow shaft, a neck portion, a ball joint connected to the neck portion and a detachable mounting ring coupling the shaft to the neck portion; and wherein the shaft is provided with local sections of weakened material, the material is adapted, with respect to its deformation characteristics, to those of the surrounding bone region and the adaptation of the longitudinal rigidity and/or resistance to bending of the shaft is effected by the targeted provision of sections of weakened material.

14 Claims, 7 Drawing Figures

HIP JOINT PROSTHESIS HAVING A HOLLOW SHAFT

BACKGROUND OF THE INVENTION

The present invention relates to a hip joint prosthesis of the type having a hollow shaft provided with locally weakened sections.

A prosthesis of this type is disclosed in DE-OS [German Laid-open application]No. 2,851,598. One drawback of this known prosthesis shaft is that it has high strength, or rigidity, with respect to the surrounding bone regions so that the shaft, because of its rigidity, constitutes a foreign body which performs movements relative to the bone that might lead to bone resorption.

Also known are perforated accessory elements for shaft prostheses, which elements serve as additional supporting elements to fix the shaft prostheses when an adhesive or bone cement is used, as disclosed in DE-OS No. 2,617,749. In this prosthesis, however, the strength or rigidity, of the entire arrangement is determined essentially by the prosthesis shaft and not by the additional supporting element. Moreover, this type of structure is extraordinarily complicated and hence expensive.

In principle, the good initial results after total hip joint replacement are presently sometimes impaired by the still unresolved problem of the cemented endoprosthesis coming loose. The natural transfer of forces from the femoral head via the femoral spur [calcar femorale] into the shaft of the femur is considerably interfered with by the installation of an endoprosthesis. The installation of a prosthesis having a collar has the drawback that nonphysiological pressure forces are generated locally at the prosthesis seat. A prosthesis without collar leads to nonphysiological circumferential stresses in the calcar femorale and in the coaxial femur region due to the wedge effect of the conical prosthesis shaft. Both the locally high pressure forces and the circumferential stresses lead to resorption of bone in the region of the calcar femorale. Due to this resorption, high circumferential stresses are also generated at a prosthesis having a collar because of the lack of support by the calcar femorale and, after a certain period of time, breaks will occur in the cement. The prosthesis thus becomes free in its upper region and moves with increasingly larger bending deformations in its cement quiver, with the result that the prosthesis is loosened completely or breaks.

SUMMARY OF THE INVENTION

In contradistinction thereto, it is an object of the present invention to provide a prosthesis whose strength behavior, and particularly its stiffness, is adapted to the bone region surrounding it.

The above and other objects are achieved, according to the present invention, by providing the hollow shaft of such a prosthesis with locally weakened regions dimensioned and located for adapting the reaction of the shaft to mechanical stress to that of the femur in which it is implanted.

The stiffness determined for different types of materials in the longitudinal direction as well as in the direction of primary bending in conventional types of prostheses are listed in the table below with respect to the cortical tube of the femur:

| Prosthesis material (type of prosthesis) | Longitudinal stiffness of prosthesis/ Longitudinal stiffness of femur | Resistance to bending of prosthesis/ Resistance to bending of femur |
|---|---|---|
| CoCr alloy | 2.11 | 1.79 |
| forged steel alloy | 2.34 | 1.98 |
| Ti alloy | 1.22 | 1.03 |
| so-called isoelastic prosthesis | 0.99 | 0.84 |
| hollow shaft prosthesis of Ti alloy without bores | 1.57 | 3.65 |
| corticalis tube of femur (spread) | 1.00 ($\pm$ 0.20) | 1.00 ($\pm$ 0.20) |
| hollow shaft prosthesis of Ti alloy, adapted by means of bores (possible breadth of variation) | 1.00 ($\pm$ 0.40) | 1.00 ($\pm$ 0.40) |

The term "longitudinal stiffness" denotes the resistance to deformation (elongation or compression) in the longitudinal, or axial, direction; the "bending" corresponds to flexure transverse to the longitudinal direction.

The above table shows that mere selection of a suitable material, such as, for example titanium or a corresponding plastic—for example, also in the so-called "isoelastic prosthesis" (disclosed, for example, in the article entitled "Erste Erfahrungen mit einer zementlosen ioselastischen Totalprothese der Hüfte" [First Experiences With a Cementless Isoelastic Total Prosthesis of the Hip] by E. Morscher and R. Mathys, published in Zorthop, 113 (1975), pages 745–749) is insufficient to adapt the resistance to bending and the longitudinal rigidity of the prosthesis to the cortical tube, or femur shaft cylinder.

A reduction of the resistance to bending as a result of the great moment of inertia of the surface area of the hollow shaft prosthesis according to the present invention is realized by the provision of weakened sections, preferably in the form of hole-shaped recesses and possibly as through bores, while simultaneously taking into account their effect on the resulting longitudinal rigidity. It has been found that the cross section of the interior as well as the exterior of the prosthesis can be weakened by means of large bores having a diameter of about 5 to 8 mm (so as to avoid notch effects) to the extent that the resulting resistance to bending corresponds to the resistance to bending existing in corresponding height regions of the cortical tube.

Further bores having a smaller diameter and provided in the anterior and/or posterior regions of the prosthesis shaft improve the development of bone substance ingrowth and possibly additionally reduce the resistance to bending but only insignificantly reduce longitudinal rigidity.

One feature of the present invention is therefore based on the realization that these additional measures are suitable to adapt the prosthesis according to the present invention separately with respect to longitudinal rigidity and resistance to bending to those characteristics of the cortical tube of the bone and thus provide favorable conditions for long-term wear without danger of the prosthesis coming loose even without the use of cement.

The prosthesis according to the present invention exhibits better yielding than a prosthesis having a solid shaft, with such yielding being adaptable to existing conditions by selection of the thickness of the prosthesis material (in a range from 1 to 3 mm). The holes—in the form of recesses or through bores—in the hollow body of the prosthesis permit the ingrowth of bone material, thus giving additional support to the prosthesis shaft according to the present invention. Filling of the hollow prosthesis body with granular bone accelerates ingrowth attachment of the prosthesis.

Further details of the present invention will become evident from the drawings.

DESCRIPTION OF THE PREFERRED EMBODIMENTS

Figure 1:
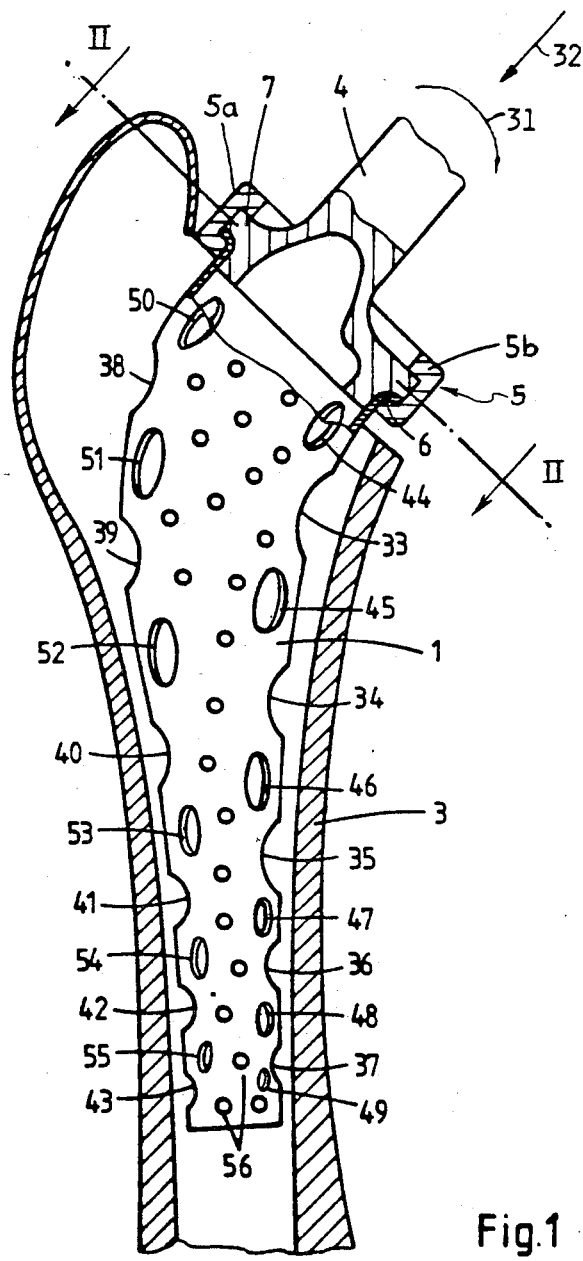
FIG. 1 is a front elevational view, partly in cross section, of a femur provided with a first embodiment of the invention.

FIG. 1 is an anterior view of a right femur 3 and shows a curved hollow shaft 1 of a hip joint prosthesis which is provided with through holes 33-43. In addition to having the illustrated curvature in the plane of the drawing, the shaft has a further, slight, curvature in a plane perpendicular thereto; this latter curvature serves to adapt the prosthesis to the left or right femur, respectively.

Figure 2:
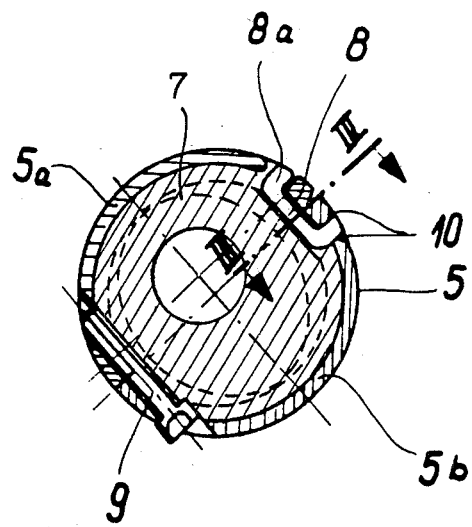
FIG. 2 is a cross-sectional view along line II—II of FIG. 1.
Figure 3:
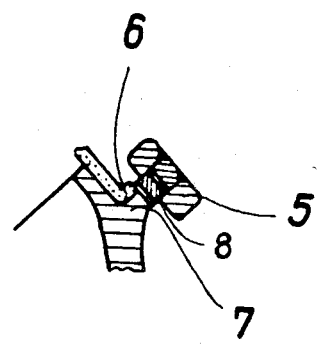
FIG. 3 is a cross-sectional detail view along line III—III of FIG. 2.

The prosthesis is inserted into femur, or thigh bone, 3 and has a neck 4 for the conventional attachment of a ball joint (not shown). A ring 5 having two halves 5a and 5b, as shown in FIG. 2, surrounds a projection 6 of the upper end of shaft 1 and a further projection 7 of the upper end of neck 4. A hook 8 is welded to ring half 5b in region 10. Its arm 8a is seated loosely in a recess of ring half 5a.

Diametrically opposite hook 8, ring halves 5a and 5b are clamped together by a machine screw 9. After loosening screw 9, half 5a can be folded away from half 5b with the result that neck 4 and thus the nonillustrated ball joint can be removed from shaft 1 for the purpose of replacing the ball joint even without removing the shaft. Hook 8 simultaneously constitutes a securing means to prevent twisting of neck 4 and the connected ball joint with respect to shaft 1. For this purpose, hook 8 bears against flattened surfaces of the peripheries of projections 6 and 7.

Figure 4:
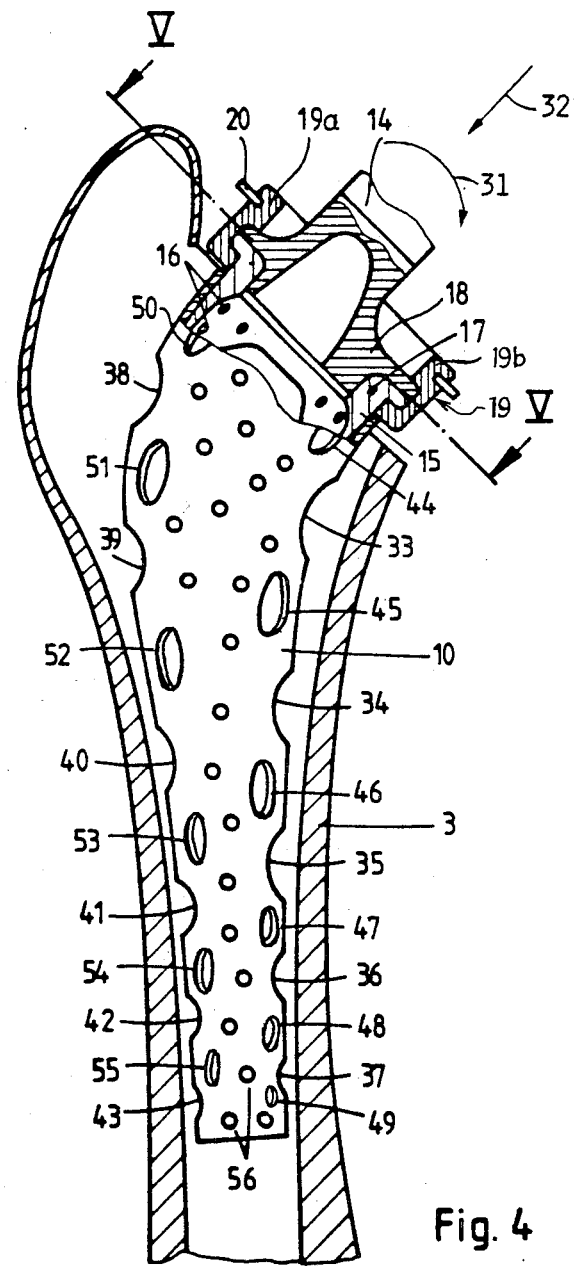
FIG. 4 is a view similar to that of FIG. 1 of a second embodiment of the invention.
Figure 5:
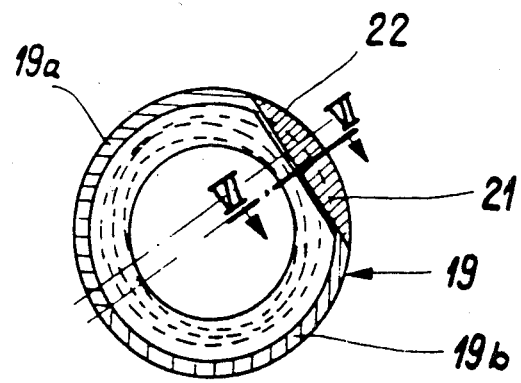
FIG. 5 is a cross-sectional view along line V—V of FIG. 4.
Figure 6:
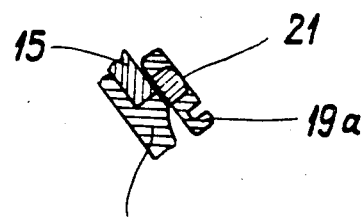
FIG. 6 is a cross-sectional detail view along line VI—VI of FIG. 5.

The embodiment of FIGS. 4 to 6 likewise includes a shaft 10, similar to shaft 1, a ball joint (not shown) and a neck 14 corresponding to neck 4. In this case, an insert 15 is provided at the upper end of shaft 10. Insert 15 and shaft 10 are welded together at points 16.

Insert 15 is provided with a projection 17 which rests against a projection 18 of neck 14. Both projections are surrounded by a ring member 19 comprising two halves 19a and 19b. The two halves of ring member 19 are held together by a spiral ring 20 which is not shown in FIGS. 5 and 6. Prevention of twisting in this case is provided by a segment 21 which is welded at 22 to the one ring section 19a and rests against correspondingly flattened peripheral portions of projections 17 and 18. Shaft 10 is made of sheet metal of a titanium alloy or a composite fiber material, such as, for example, a plastic reinforced with carbon fibers.

The prosthesis shaft 1 or 10, respectively, illustrated in the drawing figures is optimally adapted to local conditions of bone strength in the femur region. While bending stresses during wear of the prosthesis are determined primarily by forces acting essentially vertically from above, with respect to the views of FIGS. 1 and 4, with the result that a bending moment is generated, as indicated by arrow 31, which has a tendency to reinforce the illustrated, originally existing curvature, the longitudinal rigidity must be fixed with a view toward pressure forces acting in the direction of the center axis of the prosthesis. These stresses also occur from above, but such forces are introduced perpendicularly to the upper edge of the shaft region, in the direction of arrow 32.

The transfer of forces generated at the upper connection of the ball joint into the femur takes place continuously, with the reduction in size of the shaft (as well as possibly the reduction of the thickness of the shaft material) and the resulting reduction in stability corresponding to the reduction of the total forces to be transferred. The degree of strength, i.e. the weakening effect produced by provision of hole-shaped recesses of larger diameter applied in a targeted manner, is here effected in layers, with the recesses being preferably disposed in the region of the interior and exterior circumference of the major curvature as it corresponds to the shape of known femur prostheses.

Holes 33 to 43 having a larger diameter are arranged directly on the inner and outer lines of the plane of maximum curvature, with these lines extending approximately parallel to the center axis of the prosthesis. These holes decrease progressively in cross section toward the end of shaft 1 or 10 opposite the ball joint, analogously to the reduction in diameter of the associated shaft cross section. Adjacent to recesses 33 to 43 there are provided further hole-shaped recesses 44 to 55 which are arranged next to the lines of intersection of the prosthesis jacket with the plane of greatest curvature (plane of FIGS. 1 and 4) and which supplement the function of holes 33 to 43. The diameter of each of holes 44-55 is always slightly less than those of the immediately adjacent ones of holes 33-43. The hole-shaped recesses are preferably circular so as to avoid notch effects.

Further holes 56, which have a smaller diameter than holes 33-55 and are distributed over the remaining regions of the prosthesis shaft 1 or 10, take only a minor part in the strength calculations for a determination of the longitudinal rigidity of the prosthesis and primarily serve to enhance ingrowth of bone substance for reinforcement of the prosthesis seat. However, if dimensioned appropriately, these holes are suitable to reduce the resistance to bending of the prosthesis to such an extent that the prosthesis is adapted to the corresponding region of the femur if the longitudinal rigidity has already been adjusted by the dimensions of the larger recesses. In this way, it is possible to employ the present invention even with the selection of different materials.

The curvature shown in FIGS. 1 and 4 corresponds in its shape and extent to the lines of the major forces acting in the prosthesis shaft.

In order to provide even better adaptation to the different conditions in the left and right femur, an additional curvature—not shown in the drawing—is provided about an axis extending horizontally in front of or behind the plane of the drawing, i.e. the plane of the major curvature. This curvature is substantially less than the major curvature shown in the drawing and preferably affects the upper portion of the shaft.

In FIG. 6, ring 20 is not shown, and the groove for retaining that ring is visible. The prosthesis according to the invention is preferably associated with a ball joint made of a ceramic material.

In practical embodiments of the invention, the wall of shaft 1 or 10 can vary in thickness between 2 and 5 mm, the wall thickness decreasing toward the end remote from the ball joint. Alternatively, the wall can have a constant thickness in the range of 3 to 5 mm.

Preferred materials for the shaft are $Ti_6Al_4V$ or a Ti-Al-Fe alloy. The ingredient proportions of the latter alloy should be selected to provide good physiological compatibility and to correspond to the anticipated stress conditions.

The holes are distributed over the shaft in such a manner that the total cross section of the holes per annular segment (if the shaft is viewed as a series of such segments spaced along the axial direction) increases approximately linearly from the proximal end to the distal end of the shaft. While taking into consideration that a sufficient moment of bending inertia under stress should remain, approximately 0° to 60° of the shaft material is removed per annular segment for this purpose.

Figure 7:
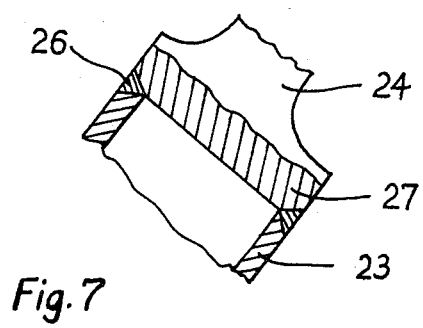
FIG. 7 is a simplified elevational view, partly in cross section, of another embodiment of the invention.

According to additional embodiments of the invention, the divided connecting rings can be eliminated, and shaft 1 or 10 can be connected to a projection on neck 4 or 14 directly by welding the projection to the shaft. It has been found that a sufficiently strong connection can be achieved in this manner. Such a connection is shown in FIG. 7 where a projection 27 of a neck 24 is welded to a shaft 23 by means of a fillet weld 26.

It will be understood that the above description of the present invention is susceptible to various modifications, changes and adaptations, and the same are intended to be comprehended within the meaning and range of equivalents of the appended claims.

What is claimed is:

1. A hip joint assembly comprising: an elongated shaft; a neck portion; a ball joint connected to one end of said neck portion; and a detachable mounting ring coupling said shaft to said neck portion; said shaft being a hollow shell constructed to be inserted and secured in an intramedullary canal of a femur; said shaft having, at a proximal end thereof, a projection extending outwardly therefrom; said shell having locally weakened means formed therein and dimensioned and positioned for adapting the response of said shaft to mechanical loading stresses of said femur; and said neck portion having an elongated stem at said one end thereof for connection to said ball joint and having, at the opposite end of said neck portion, a base protection extending outwardly therefrom, said base projection being configured to be coupled with said projection of said shaft, and said base projection being secured to said projection of said shaft by said detachable mounting ring, with said detachable mounting ring encircling said projections.

2. An assembly as defined in claim 1 wherein said shell is provided with first hole-shaped recesses establishing said locally weakened means.

3. An assembly as defined in claim 2 wherein said shell has, outside of said locally weakened means, a substantially constant thickness of between 1 and 3 mm.

4. An assembly as defined in claim 3 wherein each said first recess has a circular outline and a diameter of between 5 and 8 mm.

5. An assembly as defined in claim 4 wherein said shaft has a primary curvature in a plane containing at least a portion of the longitudinal axis of said shaft and said first recesses are located in the region of the intersections of said shell with such plane.

6. An assembly as defined in claim 5 wherein said shell is provided with a plurality of second hole-shaped recesses distributed substantially uniformly over said shell and having smaller diameters than said first recesses.

7. An assembly as defined in claim 5 wherein said shaft has a secondary curvature about an axis parallel to the plane of the primary curvature and perpendicular to the longitudinal axis of said shaft.

8. An assembly as defined in claim 2 wherein each said first recess has a circular outline and a diameter of between 5 and 8 mm.

9. An assembly as defined in claim 1 wherein said shell is constituted by a series of portions spaced apart along the longitudinal axis of said shaft, each portion being provided with respective locally weakened means for adapting the deformation characteristics of that portion to those of the (thigh bone) femur portion which will surround that shell portion.

10. An assembly as defined in claim 1 wherein said ring is composed of two ring halves.

11. An assembly as defined in claim 1 wherein the thick knees of said shell is reduced at the end of said shaft which will project into the femur.

12. An assembly as defined in claim 1 wherein the response of said shaft and of the femur is a function of the longitudinal rigidity thereof and one type of mechanical stress is in the direction of the longitudinal axis of said shaft.

13. An assembly as defined in claim 1 wherein the response of said shaft and of the femur is bending about the longitudinal axis of said shaft and one type of mechanical stress is transverse to the longitudinal axis of said shaft.

14. An assembly as defined in claim 1 wherein the response of said shaft and of the femur includes deformation parallel to the longitudinal axis of said shaft and flexure transverse to that axis and at least one type of mechanical stress includes stresses in the directions parallel and transverse to the longitudinal axis of said shaft.

* * * * *